United States Patent
Herrington et al.

(10) Patent No.: US 6,264,609 B1
(45) Date of Patent: Jul. 24, 2001

(54) ULTRASOUND APPARATUS AND METHOD FOR TISSUE CHARACTERIZATION

(75) Inventors: David M. Herrington; Liexiang Fan, both of Winston-Salem; Peter Santago, II, Clemmons, all of NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 09/396,153

(22) Filed: Sep. 15, 1999

(51) Int. Cl.$^7$ .................................................... A61B 8/00
(52) U.S. Cl. ............................................ 600/443; 600/449
(58) Field of Search ......................... 600/437, 441–447, 600/449, 450; 73/625, 626; 367/7, 11, 130; 250/341.3

(56) References Cited

U.S. PATENT DOCUMENTS

| | | |
|---|---|---|
| 4,331,021 | 5/1982 | Lopez et al. .............................. 73/1 |
| 4,542,744 | 9/1985 | Barnes ................................. 128/660 |
| 5,031,627 * | 7/1991 | Yost et al. ............................ 600/442 |
| 5,224,175 | 6/1993 | Gouge et al. ............................ 382/6 |
| 5,261,280 | 11/1993 | Matzuk .................................. 73/602 |
| 5,394,750 | 3/1995 | Matzuk .................................. 73/629 |
| 5,417,215 | 5/1995 | Evans et al. ..................... 128/660.06 |
| 5,433,206 | 7/1995 | Sabbah et al. ................... 128/661.09 |
| 5,662,109 | 9/1997 | Hutson .............................. 128/653.1 |
| 5,719,399 * | 2/1998 | Alfano et al. ...................... 250/341.3 |
| 5,720,291 | 2/1998 | Schwartz ............................ 128/661.1 |
| 5,746,209 | 5/1998 | Yost et al. ....................... 128/661.03 |
| 5,797,397 | 8/1998 | Rosenberg ...................... 128/660.04 |
| 5,836,880 | 11/1998 | Pratt ..................................... 660/443 |
| 5,860,924 | 1/1999 | Quistgaard ........................... 600/441 |
| 6,106,466 * | 8/2000 | Sheehan et al. ..................... 600/443 |

OTHER PUBLICATIONS

Abstract, L. Fan et al., *A Spatiotemporal Strategy for Automated Analysis of Vasodilator Response*, Computers in Cardiology, Sep. 13–16, 1998, Cleveland, Ohio, p. 44.

Abstract, L. Fan et al., *Simulation of B–Mod e Ultrasound to Determine Features of Vascular Vessels for Image Analysis*, Computers in Cardiology, Sep. 13–16, 1998, Cleveland, Ohio, p. 45.

* cited by examiner

Primary Examiner—Peter Vo
Assistant Examiner—Ali M. Imam
(74) Attorney, Agent, or Firm—Dann, Dorfman, Herrell & Skillman, P.C.

(57) ABSTRACT

The present invention relates generally to a medical device, and more particularly to ultrasound apparatus and methods for the identification and characterization of tissues, tissue transitions and tissue constituent structures.

5 Claims, 7 Drawing Sheets

ULTRASOUND APPARATUS AND METHOD FOR TISSUE CHARACTERIZATION

FIELD OF THE INVENTION

The present invention relates generally to a medical device, and more particularly to ultrasound apparatus and methods for the identification and characterization of tissues and their constituent structures.

BACKGROUND OF THE INVENTION

Methods and apparatus which utilize ultrasound energy for diagnostic imaging of targeted anatomical organs and blood flow are known. Typically, ultrasound energy is directed into and scattered from body tissues. The amplitude envelope of the scattered ultrasound energy known as an echo is detected and displayed to form an image which characterizes the targeted structures.

Virtually all commercial medical ultrasound imaging systems form images from the amplitude envelope of the scattered ultrasound energy that is returned by an interface of different organ tissue types having different acoustic impedances. Although the prior art systems attempt to delineate various body organs, they cannot identify different types of organ tissue or identify various structures within the same tissue. Further, these systems fail to make use of the phase information of the scattered ultrasound energy which is particularly useful to image and identify tissues and their various constituent structures.

SUMMARY OF THE INVENTION

The present invention is an ultrasound apparatus and method for tissue characterization. The invention uses parametric imaging where the parameter or feature of interest in the tissue is the randomness of the scatterers produced by the tissue relative to each other in a region of interest in the tissue. A parametric image forming a feature space is rendered and gradients in the feature space can be used to identify transitions from one tissue type to another.

The invention establishes a physical model of preselected tissue that is used to simulate an ultrasound image formation process. The invention simulates an ultrasound image structure comprising the pre-selected tissue. In addition, the invention can compare the simulated data with scanned images of actual pre-selected tissue. Further, the invention can detect tissue transitions using gradient or other edge detection techniques in a feature space where the substrate for the algorithm is a metric of randomness of the scatterers in the region of interest.

Thus, the invention includes three distinct components that may be used separately or in combination to determine tissue structure and establish boundaries from this structure.

First, the invention utilizes the randomness of the scatterers to build a parametric image of the tissue from the rf signal. This image, or map, illustrates tissue structure and tissue boundaries. Parametric descriptions and metrics using randomness of the scatterers, can be used to characterize the tissue. The standard gain control (SGC) map defined herein is a specific example of such a metric.

Second, boundary detection can be accomplished by applying gradient or other edge detection methods to the parametric or feature map in order to quantify spatial characteristics and dimensions of the tissue.

Third, a method of simulating tissue structure and the response of the tissue to ultrasound energy has been established. The simulated tissue structure can be compared to the tissue structure determined from an actual ultrasound scan in order to determine tissue type and tissue boundaries.

BRIEF DESCRIPTION OF THE DRAWINGS

For the purpose of illustrating the invention, specific embodiments are shown in the drawings, however, it is understood that this invention is not limited to the precise arrangements and instrumentalities shown.

DETAILED DESCRIPTION OF THE INVENTION

Figure 1:
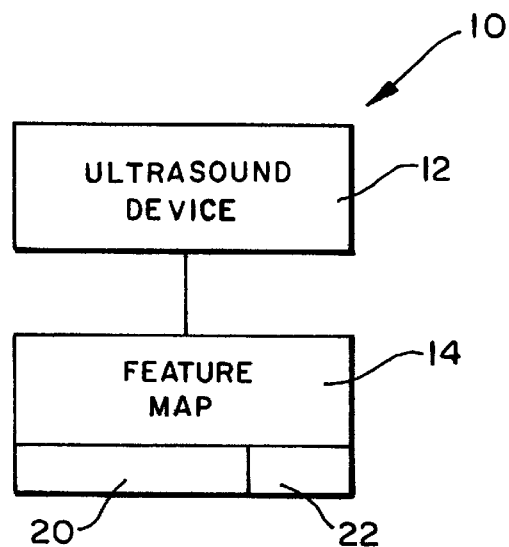
FIG. 1 illustrates a block diagram of an ultrasound system according to the present invention.

Referring now to the drawings, wherein like numerals indicate like elements, there is shown in FIG. 1 an illustration of a block diagram of an ultrasound system 10 according to the present invention. The system 10 shows a B-mode ultrasound device 12 using data corresponding to a feature map 14 for boundary detection of tissues and their constituent structures. The feature map 14 contains individual tissue data of predetermined tissue interfaces which were simulated and analyzed by modeling distributed scatterers in the form of an SGC map to identify a specific tissue feature for image analysis.

Information related to, and quantitative measurement of, vascular tissue and constituent structures in vascular tissue from B-mode ultrasound images would be particularly useful for physicians and researchers to determine tissue pathology. Further, parameters such as the diameter of a vessel wall and the thickness of vessel walls provide significant information for clinical and research applications.

Referring to FIG. 1, the specific method developed and described here employs a physical model 20 of preselected tissue 22 that is used to simulate the image formation process. The physical model 20 contains information related to the composition of the constituent structures comprising the pre-selected tissue. This information is then used to simulate an expectant ultrasound image. This simulation process provides insight into the B-mode ultrasound image formation process and serves to validate the physical model made by comparing the simulated data with scanned images of actual pre-selected tissue.

The tissue physical model 20 is based on the histological structure of the muscular artery. The artery wall consists of adventitia, media, and intima layers. The adventitia layer is composed of the connective tissues, these tissue cells have various physical properties and are irregularly located in space. The media layer is composed of smooth muscle cells, where each individual cell is approximately the same size and the spatial distribution is more regular (less random) than the cells in the adventitia. The intima layer is very thin, typically only one cell in width.

When an ultrasound pulse propagates through the vessel wall, it is scattered by the heterogeneous sites in the wall. The intensity of the scattered wave is related to the variation of the density, compressibility, and distance from the transducer, while the timing of the return signal is related to the spatial distribution of the scatters. Variability (or randomness) in the spatial distribution of the scatters is the central tissue characteristic that this invention is designed to detect. This feature is highly variable from tissue type to tissue type and therefore provides a means to detect transitions from one tissue type to another. Applying gradient base edge detection to this feature space thereby provides a means to quantify dimensional aspects of different tissues.

Figure 2:
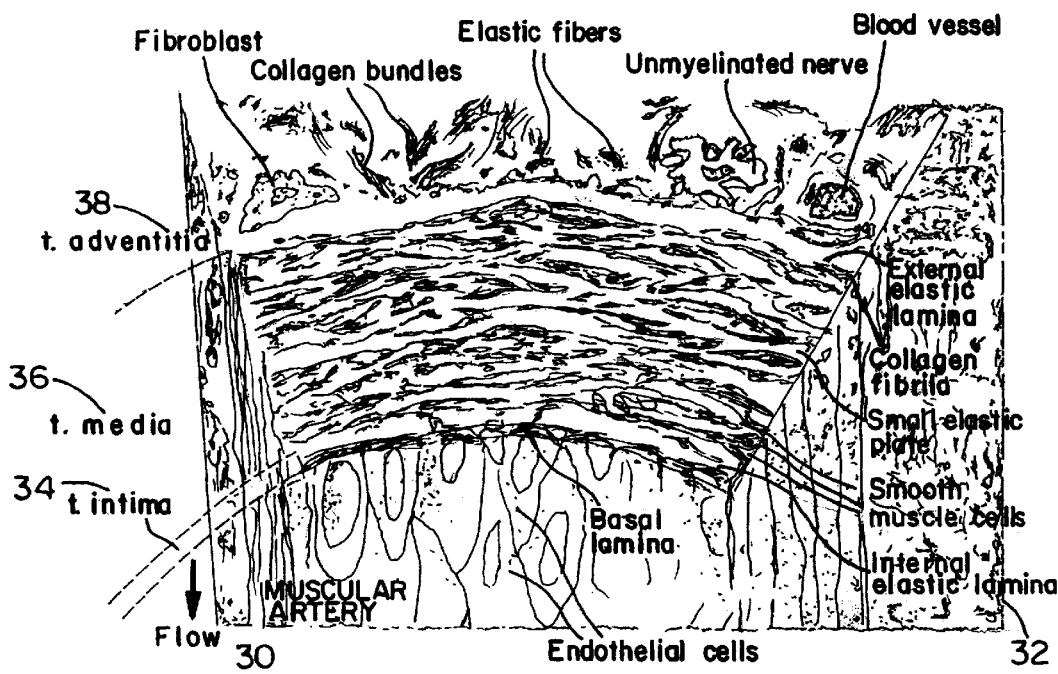
FIG. 2 illustrates a blood artery and the type of constituent structures that are to be detected by the present invention.

As an example, FIG. 2 illustrates the structures and transitions that can be detected and rendered by the invention such as a blood artery 30 and its constituent structures known as lumen 32, intima 34, media 36, and adventitia 38. Due to the inhomogeneity of the artery and the constituent structures in the artery 30, the ultrasound energy returned by these structures cannot be treated as a simple reflection of energy from the interface of the different constituent structures.

A solution of the complex wave equations is achieved by use of the physical model 20. This can be accomplished by selecting specific parameters used in the physical model 20. For example, the following assumptions can be made for arterial tissue:

(1) Each tissue cell is represented by its spatial position Ri related to the transducer and the differential backscatter cross-section (DBC), $\sigma_i$;

(2) Red blood cells are assumed to have a constant DBC and are randomly distributed in the lumen with a hematocrit of 46%;

(3) The smooth muscle cells in the media have a constant DBC and are regularly distributed in space; and (4) The connective tissue cells in the adventitia have various DBCs and are randomly positioned in a structural grid.

Figure 3:
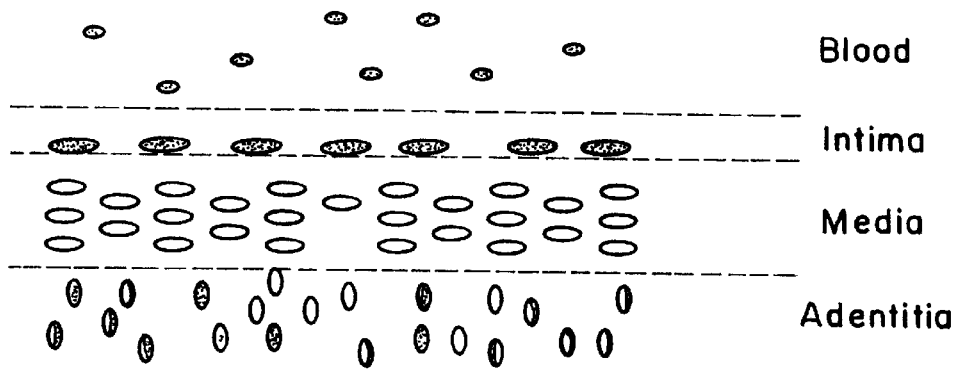
FIG. 3 illustrates a simplified and abstracted physical model according to the present invention.

A simplified and abstracted physical model based on these assumptions is depicted in FIG. 3.

When an acoustic pulse is applied to the model the backscatter signal is determined by:

$$S(t) = \sum_i \frac{\sqrt{\sigma_i}}{|R_i|} p\left(t - 2\frac{|K \cdot Ri|}{c}\right) \quad \text{Eq. (1)}$$

where $\sigma_i$ is DBC of the i-th scatter, and p( ) is a function of the transmitted signal. K is the wave number, Ri is the vector from a transducer to the scatterer (constituent structure), and c is the speed of sound in soft tissue. In addition, the term $2|K \cdot Ri|/c$ represents a delay which corresponds to constructive and destructive contributions made to the received signal S(t).

In the physical model 20, a pre-selected pulse signal is used such as, but not limited to, a 10 MHz center frequency having a 2 MHz bandwidth and a pulse width of 4 cycles. In addition, the ultrasound energy is assumed to be directed in a beam having a lateral width that is 6 times the wavelength of the ultrasound wave in tissue.

Figure 5A:
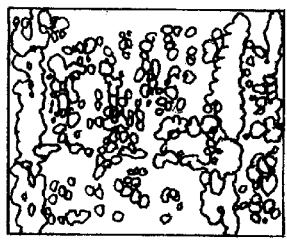
FIGS. 5a and b illustrate B-mode ultrasound images of brachial artery.
Figure 5B:
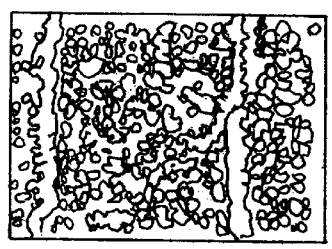
Figure 4A:
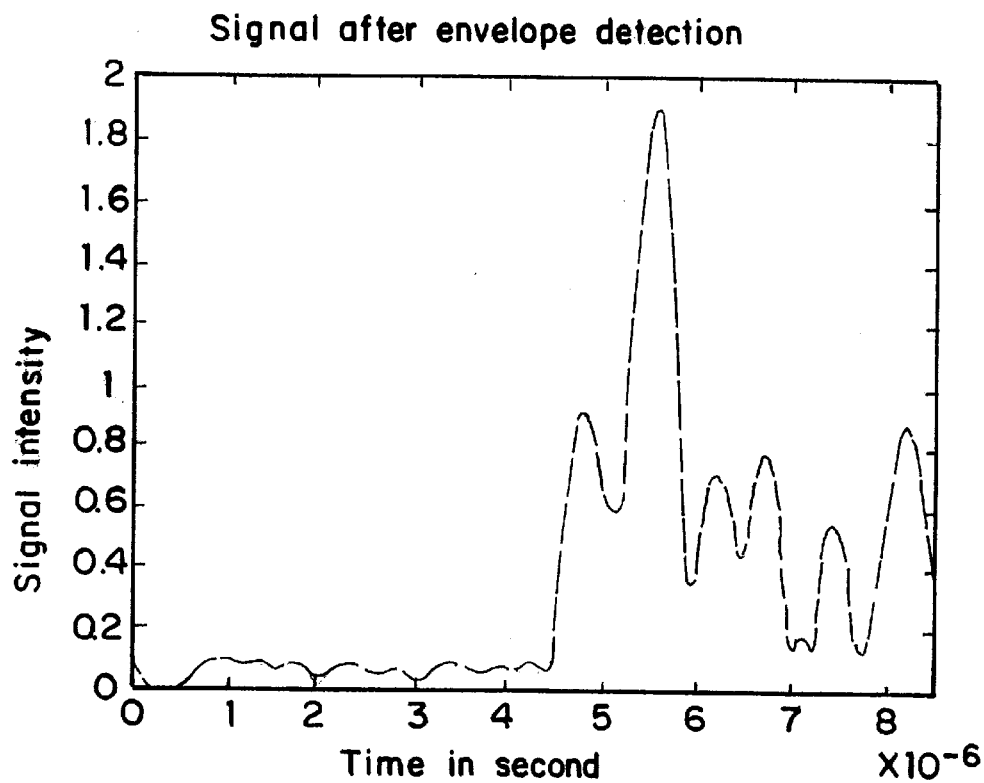
FIGS. 4a and c illustrate the results of a one-dimension simulation according to the present invention.
Figure 4B:
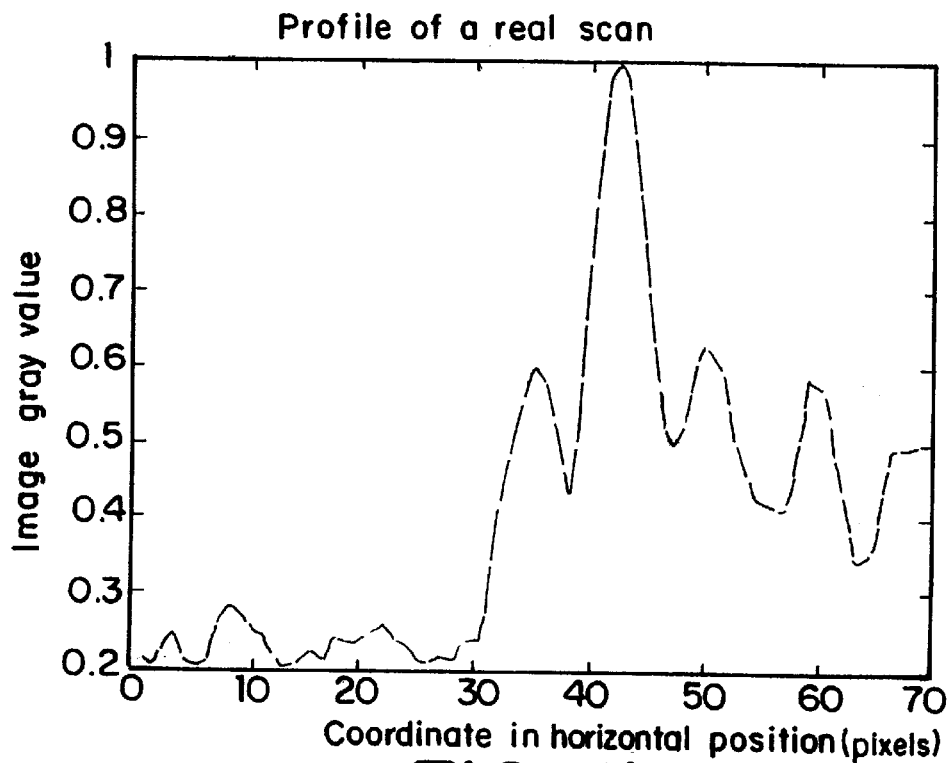
FIGS. 4b and d illustrate a brightness profile from real B-mode images.
Figure 4C:
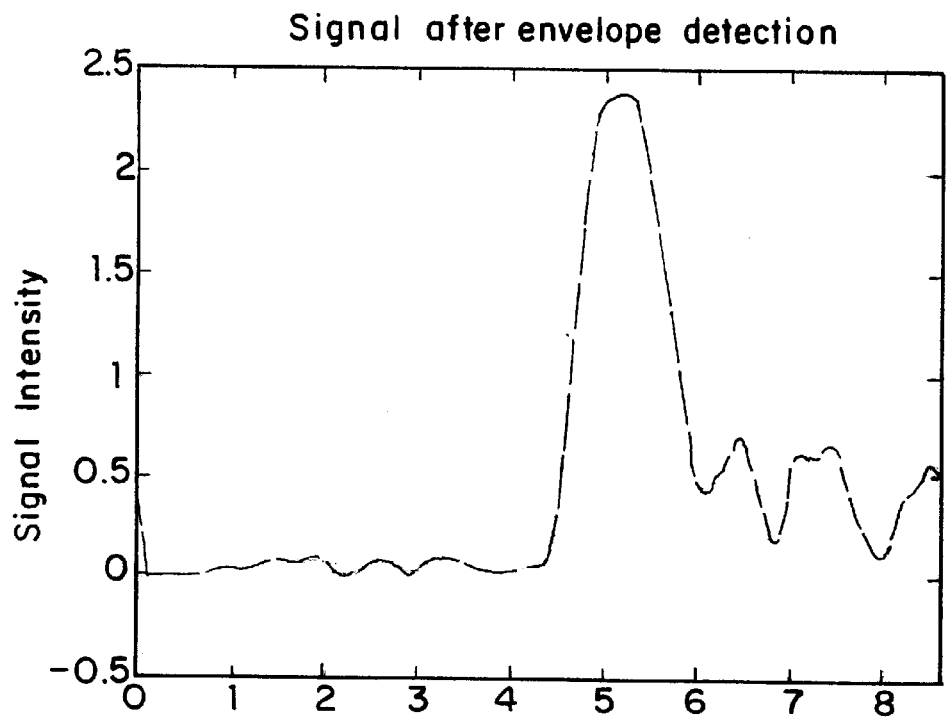
Figure 4D:
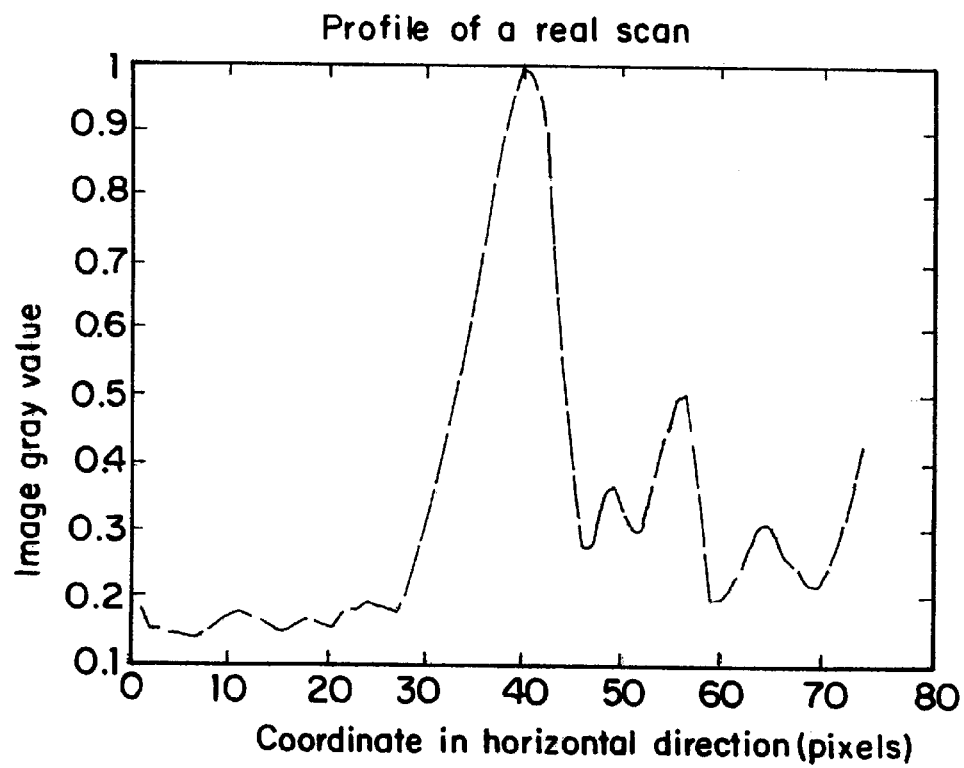

Using this signal, the present invention can produce single and multi-dimensional simulated images of pre-selected tissue structures. For the arterial tissue described above, the result of a one-dimension simulation will produce a backscatter signal as shown in FIGS. 4a and 4c. FIGS. 4b and 4d correspond to the horizontal profile of the crude images produced by conventional ultrasound as shown in FIGS. 5a and 5b.

In addition, the simulation can provide for pre-selected intima-media thicknesses. For example, a thickness of 0.6 mm was used in FIG. 4a, and 0.3 mm in FIG. 4c.

Figure 6:
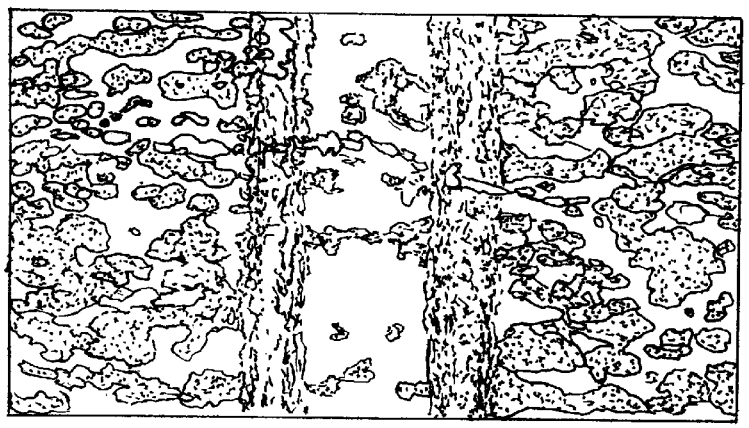
FIG. 6 illustrates a two-dimension simulation for arterial tissue according to the present invention.

A two-dimension simulation for the same arterial tissue described above is shown in FIG. 6. This simulation was produced for muscle cells having a distance of 30 µm. This result can be compared with conventional ultrasound images shown in FIGS. 5a and 5b which demonstrate the fusion of the interface between the lumen, intima, media, and adventitia.

In order to quantify the vessel structure, determining boundaries between different tissues is useful, and gradient based edge detection method are often used to find these boundaries. As shown in FIGS. 5b (real scan data) and 6 (simulation results) illustrate fusion of blood intimal and media adventitial boundaries. In this setting, the gradient based edge detection method fail to identify the boundaries of interest. The data in FIGS. 4(c) and 4(d) also show fusion of the boundary interfaces. If the gradient operator is applied, the peak of the gradient value may not be at the same location as the real boundary. This results in the inaccurate measurement of the diameter and wall thickness of the vessel. In FIG. 4d, the two-layer structure cannot be identified demonstrating the phenomena of the real scans shown in FIG. 5b. The simulation illustrates the effect of the spatial structure of adjacent tissues on the image of tissue interfaces and suggests a mechanism to deduce the spatial property from the A-line RF signal.

Given the distribution of $N_o$ scatters in either one or two dimensions, the frequency response of this distribution of scatterers can be obtained by deconvolving the received signal, S(t), with the transmitted pulse p(t). The Fourier transform of S(t) is obtained using equation (1) as follows:

$$S(\omega) = P(\omega) \cdot \sum_{i=0}^{N_0-1} \frac{\sqrt{\sigma_i}}{R_i} \exp\left(-j2\frac{|K \cdot Ri|}{c}\omega\right) \quad \text{Eq. (2)}$$

Figure 7:
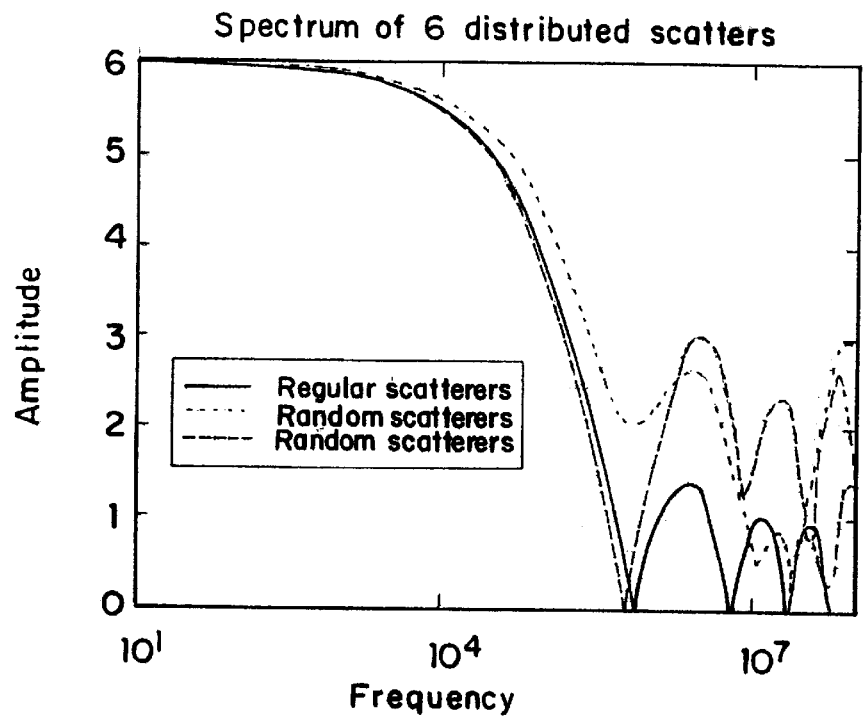
FIG. 7 illustrates a signature of scatterer distribution produced by the present invention.

Accordingly, the signature of the distribution of the scatterers is represented as:

$$T(\omega) = \sum_{i=0}^{N_0-1} \frac{\sqrt{\sigma_i}}{R_i} \exp\left(-j2\frac{|K \cdot Ri|}{c}\omega\right) \quad \text{Eq. (3)}$$

and are shown in FIG. 7. A different spectrum of scattered energy is produced by random DBCs and Rs. This property is used to identify the boundary between the smooth muscle and the adventitia. The differential backscattering cross-section (DBC) for the adventitial layer is used as a reference. The ratio of the differential backscattering cross-section of all tissues to this reference is unitless, and presented by dB. So the relative DBC for the adventitia is 0 dB and the DBC for smooth muscle is −3 dB.

A novel representation of the tissue cell distribution is achieved using a feature defined as the spectrum gravity center, $$SGC = \frac{\int_\omega \omega |T(\omega)| d\omega}{\int_\omega |T(\omega)| d\omega'} \quad \text{Eq. 4}$$

where ω is the selected frequency window. The implicit idea of the SGC map is that the randomness of distribution of the scatterers increases the high frequency component of the spectrum. Biologically, different distribution properties of the tissue cells may be used as a signature of the tissue. The spectrum of regular distribution of scatterers is a sinc function and has low SGC value. Randomly distributed scatterers result in higher SGC values.

Figure 8A:
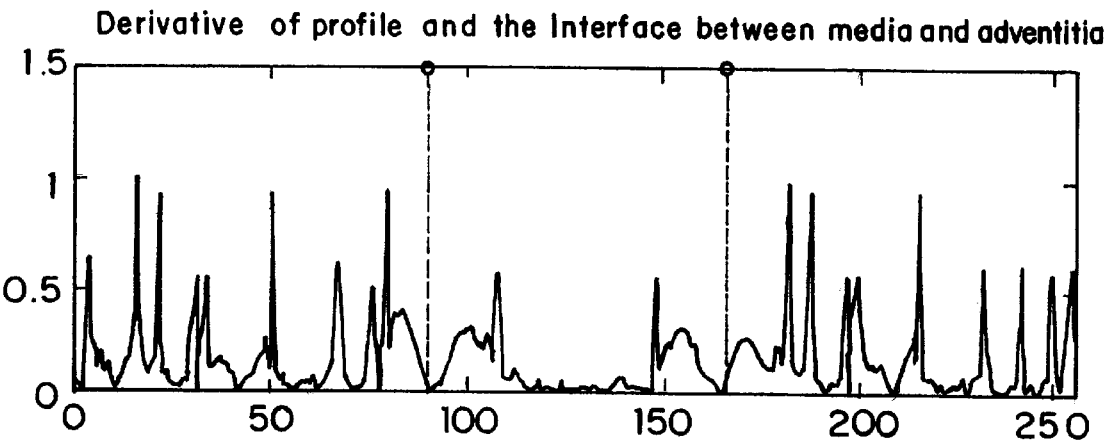
FIGS. 8a and b illustrate the derivative of the simulated image brightness profile and the SGC map profile.
Figure 8B:
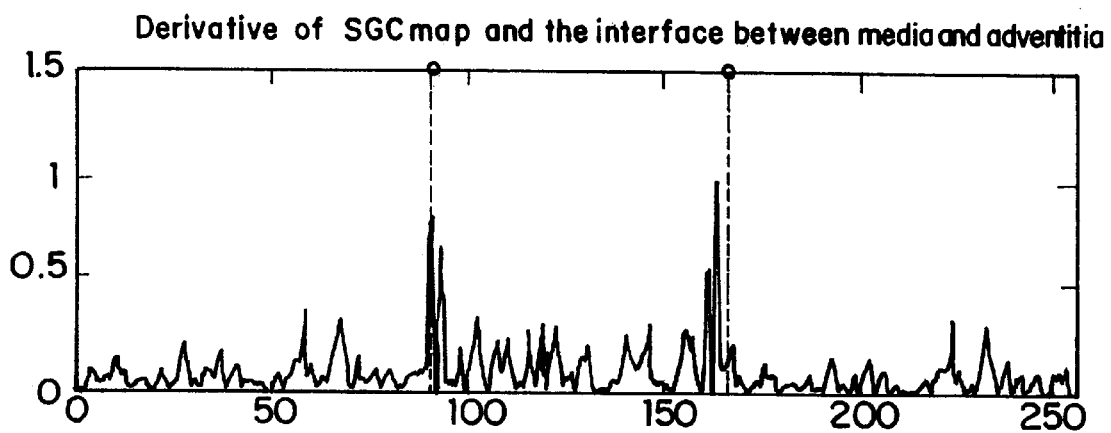

The boundary detection is based on the gradient image derived from the SGC map. A cost function is defined in terms of gradient and curvature of the boundary, and a dynamic programming method is used to minimize the cost function. FIG. 8(a) shows the absolute values of the derivative of the simulated image brightness profile; FIG. 8(b) shows the derivative of SGC map profile. Profile data are from the center horizontal lines of FIG. 6 and FIG. 9. The interface between the media and adventitia is marked by a dotted spike. The peaks of derivative of SGC map profile are much stronger and closer to the interfaces than that of the image data brightness profile.

The physical model 20 provides a useful method for determining image analysis features including SGC which is responsive to the distribution of the scattered ultrasound energy. The use of SGC improves the resolution of tissue structure imaging particularly for vessel boundary detection applications. In our model, the tissue cells in the blood and adventitia are more randomly distributed than those in the smooth muscle tissue. So the SGC value in smooth muscle tissue is expected to have low value. In the lumen area, because the DSCS value is much lower than those of the other two tissues, the SGC values are also lower than that of the adventitia.

A single SGC value corresponds to a set of scatterers. We follow the idea of a B-mode image, and display the SGC value as a function of depth (or time) of the ultrasound pathway for each scan line. The matrix we obtain is called an SGC map. Compared with the integrated backscatterer, the SGC weights the spectrum by frequency, which means that, for different spectrum shapes, the SGC may vary due to the weight factor ω. However, the integrated backscatterer may give the same value if the area of the spectrum is the same.

Assuming the maximum depth of the observation of one scan line is Dmax, the maximum time of the observation of one scan line is 2Dmax/c. The support of the baseband signal $S_{BB}$ (t) is [0, (t)]. Assuming the resolution of the imaging system is the same as the pulse length, then the length of the data segment used to obtain one SGC should be one pulse length, the time interval of this segment is twice the pulse length. We compute the SGC map by sliding the time axis, that is to say, the |T(w)| can be represented as |T(w, t)| and $S_{BB}(\omega)$ as $S_{BB}(\omega,t)$.

To obtain the spectrum |T(ω, t)|, we can take the magnitude of $S_{BB}(\omega, t)$. and divide it by the spectrum of the pulse wave |A(ω,t)|. However, in practice a noise term needs to be taken into consideration in $S_{BB}(\omega, t)$. That is $$S_{BB}=(\omega,t)=A(\omega)|T(\omega,t)|e^{j\angle T(\omega,t)}+N(\omega) \quad \text{Eq. 5}$$

There are many approaches to restore |T(ω, t)|, such as the inverse filter, the Wiener filter, iterative methods, projection of convex set methods, and the Kalman filter. In a preferred mode, the Wiener filter is used because of enhanced real-time implementation.

We estimate |T(ω, t)| by use of the equation:

$$T(\omega, t) = \frac{S_{BB}(\omega, t)A^*(\omega)}{A(\omega)A^*(\omega) + \gamma[1 - \cos(\omega)]^2} \quad \text{Eq. 6}$$

Figure 9:
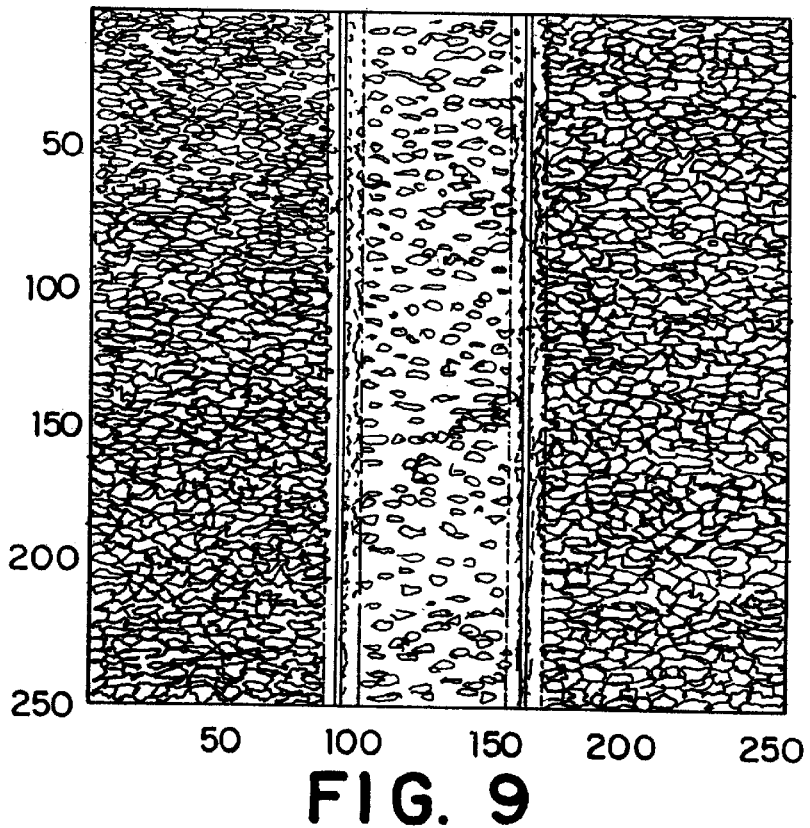
FIG. 9 illustrates a sample SGC map without noise according to the present invention.

A(ω) can be obtained from the manufacturer of the measuring instrument or by measuring the response of a point target embedded in a homogeneous medium. Since we are now dealing with a simulated image, we know the exact A(ω). One sample of the SGC map without noise is shown in FIG. 9.

FIG. 8 illustrates the absolute values of the derivative of the simulated image brightness profile of the SGC map. The profile data is represented by the center horizontal lines from the synthetic image and its SGC map. The actual interface between the media and adventitia is represented by dashed lines. The peaks of derivative of SGC map profile are much stronger and closer to the interfaces than that of the image data brightness profile. Specifically, FIG. 8a a represents the profile gradient from the synthetic image and FIG. 8b represents the profile gradient from the SGC map.

It is to be understood that an estimate of transitions from one tissue type to another can be achieved from any gradient based boundary or edge detection algorithm when applied to the SGC map or some derivative thereof using the metric of randomness to acquire an estimate of tissue transition.

Figure 10:
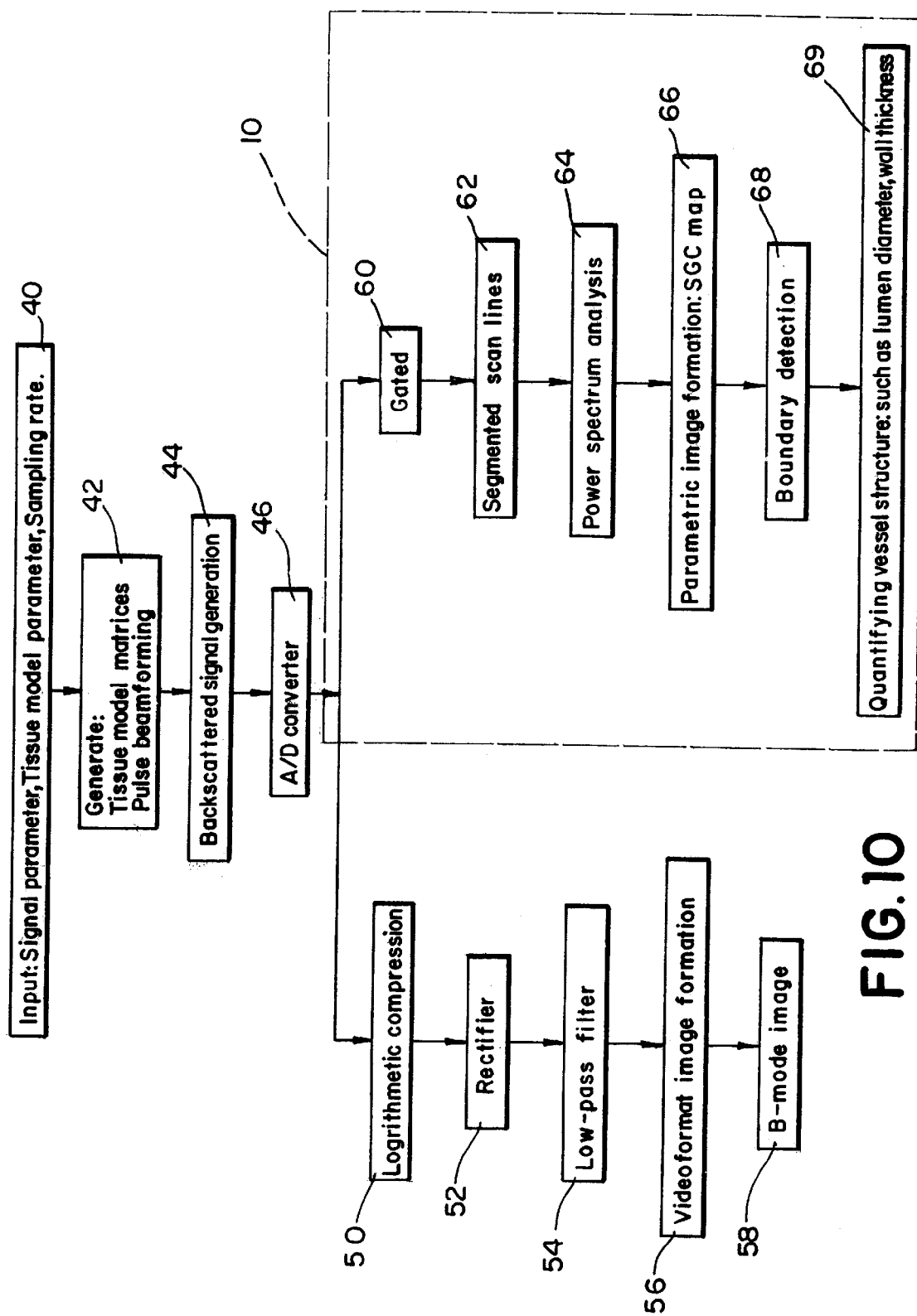
FIG. 10 illustrates a flow diagram of a method for tissue characterization according to the present invention.

FIG. 10 illustrates a flow diagram of a method for tissue characterization according to the present invention. A method and apparatus is provided to allow the operator to input 40 signal parameters such as the bandwidth central frequency and the number of cycles. A generator 42 creates scatter cells and stores them in matrices in a computer memory. The discretization of the pulse beam width, pulse length, and the pattern directivity are also stored in a matrix. The backscatter signal is generated 44 by means of Equation 1. The backscatter signal is then digitized 46 by an A/D converter.

In conventional B-mode ultrasound, a logrithmatic operation 50 is applied to the to the digital signal. A rectifier 52 takes the absolute value of the digital signal after logrithmatic compression 50, and then passes it through a low-pass filter 54. Several scan lines are combined to generate one video scan line 56. The combination of the video scan lines produces the B-mode image 58.

In the present invention, the digitized backscatter signal 44 from the A/D converter 46 is gated 60 to form scan lines. Each scan line is divided into a number of segments 62. A power spectrum analysis 64 is applied to each segment and a parametric image formation 66 producing the SGC map is generated from the power spectrum. A boundary detection algorithm 68 is then applied to the SGC map. Vessel structure is then Quantified 69. The vessel structure quantities, such as lumen diameter and wall thickness, are calculated from the boundary detection results.

For example, a method and apparatus for tissue characterization in a region of interest may include or perform some or all of the following steps, gating digitized backscatter signals to form scan lines, segmenting each scan line into a pre-determined number of segments, analyzing the power spectrum of each segment, forming a parametric image to produce an SGC map, applying a boundary detection algorithm to detect tissue boundaries by means of the SGC map, and quantifying the vessel structure.

The invention has three distinct components that may be used separately or in combination to determine tissue structure and establish boundaries from this structure.

First, the invention utilizes the randomness of the scatterers to build a parametric image of the tissue from the rf signal. This image, or map, illustrates tissue structure and tissue boundaries. Parametric descriptions and metrics using randomness of the scatterers, can be used to characterize the tissue. The SGC map defined herein is a specific example of such a metric.

Second, boundary detection can be accomplished by applying gradient or other edge detection methods to the parametric or feature map in order to quantify spatial characteristics and dimensions of the tissue.

Third, a method of simulating tissue structure and the response of the tissue to ultrasound energy has been established. The simulated tissue structure can be compared to the tissue structure determined from an actual ultrasound scan in order to determine tissue type and tissue boundaries.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all chances and modifications that are within the scope and spirit of the invention as set forth in the claims.

What is claimed is:

1. A method for tissue characterization in a region of interest in a body comprising the steps of:

establishing a physical model of pre-selected tissue that is used to simulate an ultrasound image formation process;

simulating an ultrasound image structure comprising the pre-selected tissue;

comparing the simulated data with scanned images of actual pre-selected tissue; and distinguishing gradients in the feature space to identify transitions between different tissue types.

2. The method of claim 1 wherein said simulating an ultrasound image comprises the simulation of transmitting pulses of ultrasound energy into a body, receiving pulses of returned ultrasound energy for said region of interest in said body, digitizing said pulses of returned energy, and computing the power spectrum by performing a Fast Fourier Transform on said digitized pulses of returned energy; and determining the Fourier energy in each of a plurality of selected Fourier frequency bands of the power spectrum of said digitized pulses.

3. A method for tissue characterization in a region of interest in a body comprising the steps of:

establishing a physical model of pre-selected tissue that is used to simulate an ultrasound image formation process;

simulating an ultrasound image structure comprising the pre-selected tissue;

comparing the simulated data with scanned images of actual pre-selected tissue; and detecting tissue transitions using gradient based edge detection in a feature space where the substrate for the algorithm is a metric of randomness of the scatterers in the region of interest.

4. A method for tissue characterization in a region of interest in a body comprising the steps of:

gating digitized backscatter signals to form scan lines;

segmenting each scan line into a pre-determined number of segments;

analyzing the power spectrum of each segment;

forming a parametric image to produce a standard gain control (SGC) map;

applying a boundary detection algorithm to detect tissue boundaries by means of the SGC map; and quantifying the tissue structure.

5. An apparatus for tissue characterization in a region of interest in a body comprising:

a gating device for digitized backscatter signals to form scan lines;

a segmenting device for segmenting each scan line into a pre-determined number of segments;

an analyzer for analyzing the power spectrum of each segment;

forming a parametric image to produce a standard gain control (SGC) map;

applying a boundary detection algorithm to detect tissue boundaries by means of the SGC map; and quantifying the tissue structure.

* * * * *